United States Patent [19]

Beer et al.

[11] 4,154,970

[45] May 15, 1979

[54] TREATMENT OF BUTANEDIOL OBTAINED AS A CONDENSATE DURING THE MANUFACTURE OF POLYBUTYLENE TEREPHTHALATE

[75] Inventors: Ludwig Beer, Ludwigshafen; Heinrich Mandel, Frankenthal, both of Fed. Rep. of Germany

[73] Assignee: BASF Aktiengesellschaft, Ludwigshafen, Fed. Rep. of Germany

[21] Appl. No.: 913,643

[22] Filed: Jun. 8, 1978

[30] Foreign Application Priority Data

Jun. 24, 1977 [DE] Fed. Rep. of Germany ....... 2728407

[51] Int. Cl.$^2$ .............................................. C07C 29/24
[52] U.S. Cl. ..................................... 568/868; 568/871
[58] Field of Search .................................. 568/868, 871

[56] References Cited

U.S. PATENT DOCUMENTS

| | | | |
|---|---|---|---|
| 2,793,235 | 5/1957 | Jenkinson | 568/871 |
| 3,859,368 | 1/1975 | Kollar | 568/868 |

FOREIGN PATENT DOCUMENTS 166184 10/1953 Australia ................................. 568/871

*Primary Examiner*—Joseph E. Evans
*Attorney, Agent, or Firm*—Keil & Witherspoon

[57] ABSTRACT

A process for treating butanediol obtained as a condensate during the manufacture of polybutylene terephthalate, wherein an alkali metal alcoholate or alkali metal hydride is added to the condensate at an elevated temperature. After purification, the butanediol obtained is re-used for the manufacture of polybutylene terephthalate.

6 Claims, No Drawings

TREATMENT OF BUTANEDIOL OBTAINED AS A CONDENSATE DURING THE MANUFACTURE OF POLYBUTYLENE TEREPHTHALATE

The present invention relates to a process for the treatment of butanediol, which has been obtained as a condensate in the manufacture of polybutylene terephthalate, with an alkaline reagent.

It is known (cf. German Laid-Open Application DOS 2,214,775 and DOS 2,514,116) to manufacture polybutylene terephthalate by trans-esterifying dimethyl terephthalate with 1,4-butanediol or directly esterifying terephthalic acid with 1,4-butanediol, and then polycondensing the resulting bis-hydroxybutyl terephthalate and its oligomers, with elimination of 1,4-butanediol, at an elevated temperature under reduced pressure. During polycondensation, the 1,4-butanediol formed by elimination, and the excess 1,4-butanediol present, is distilled off at an elevated temperature under reduced pressure. Because of the very low pressures which must be used during the polycondensation, the vapors leaving the reactor not only contain 1,4-butanediol but also small amounts of bis-hydroxybutyl terephthalate and its oligomers, as well as catalyst-containing constituents and products of unknown composition. Fine droplets of polybutylene terephthalate may also be entrained. The vapors from the polycondensation are condensed, for example on heat exchange surfaces or, in particular, by means of injection condensers, located upstream from the vacuum units. These concomitant materials in the butanediol vapors are in part solids, which are only sparingly soluble in cold or moderately warm butanediol. Accordingly, they separate out as solids when condensing the vapors in the circulation system of the condenser, and these solids cause considerable problems, particularly in continuous operation but also in batchwise operation, for example by blocking the dispersing nozzles of the condensers or by depositing on the cooling surfaces.

Similar problems due to solids separating out of condensed ethylene glycol in the manufacture of polyethylene terephthalate are prevented by adding an alkali metal hydroxide or alkali metal carbonate, as described in U.S. Pat. 2,793,235. However, to ensure effective dissolution of the polyesters, at least stoichiometric amounts of alkali metal hydroxide must be used. The resulting hydrolysis product dissolves in the ethylene glycol. If 1,4-butanediol resulting from the manufacture of polybutylene terephthalate is treated similarly, it is found that even after several hours' treatment the solids which have separated out cannot be brought into solution.

It is an object of the invention to provide a method of treating butanediol, obtained as a condensate in the manufacture of polybutylene terephthalate, in such a way that no solid separates out.

We have found that this object is achieved by a process for treating butanediol obtained as a condensate in the manufacture of polybutylene terephthalate, wherein an alkali metal alcoholate or alkali metal hydride is added to the condensate at an elevated temperature.

The novel process has the advantage that the solids contained in the butanediol condensate are dissolved in a simple and effective manner, so that no problems arise in the condensers. The novel process has the further advantage that less than the stoichiometric amount of the alkaline reagents of the invention is required. This is surprising inasmuch as the alkali metal alcoholates are compounds whose chemical activity frequently corresponds to that of the alkali metal hydroxides. The amount of alkali metal alcoholate required to dissolve completely the solids in the butanediol is lower, by an order of magnitude, than the amount of sodium hydroxide which is required to dissolve solids in ethylene glycol originating from the manufacture of polyethylene terephthalate.

The 1,4-butanediol which requires treatment is obtained as a condensate from the manufacture of polybutylene terephthalate. In this latter process, for example, dimethyl terephthalate is used as the starting material and is transesterified with 1,4-butanediol in the presence of a transesterification catalyst at from 160° to 230° C., and the resulting bis-hydroxybutyl terephthalate is condensed, in one or more stages, at from 230° to 270° C. under a pressure down to 0.1 mm Hg. It is also possible to have present up to 40 mole%, based on dimethyl terephthalate and/or 1,4-butanediol, of other polyester-forming starting materials and the term "polybutylene terephthalate" includes polyesters obtained from such mixtures. Examples of suitable starting materials are dimethyl esters of alkanedicarboxylic acids of 4 to 12 carbon atoms or of isophthalic acid, and alkanediols or cycloalkanediols of up to 8 carbon atoms. Examples of suitable processes are described in German Laid-Open Applications DOS 2,514,116 and DOS 2,214,775. Condensates formed in the manufacture of polybutylene terephthalate contain, in addition to butanediol, up to about 20% by weight of solids. Furthermore, if other diols are also present as esterforming components, these may also be present in the condensate in accordance with their proportion, for example in an amount of up to 40% by weight. The butanediol condensates which require treatment are essentially formed during the precondensation stage and the final condensation stage. A typical condensate obtained in the manufacture of polybutylene terephthalate essentially contains 1,4-butanediol and has a solids content of from 3 to 6% by weight. The proportion of solids insoluble at room temperature is from about 1 to 3% by weight.

The treatment is carried out by adding an alkali metal alcoholate or alkali metal hydride. Alkali metal alcoholates derived from alkanols or cycloalkanols of up to 10 carbon atoms, especially of up to 7 carbon atoms, or from alkanediols of 2 to 6 carbon atoms, are particularly preferred. Sodium alcoholates derived from alkanols of 1 to 4 carbon atoms have acquired particular industrial importance. Examples of suitable compounds are sodium methylate, sodium ethylate and sodium butylate.

Advantageously, the amount of alkali metal alcoholate or alkali metal hydride added to the condensate to be treated is from 0.01 to 0.2% by weight, preferably from 0.01 to 0.1% by weight. If too small an amount is selected, the solution process is too slow whilst if too large an amount is selected difficulties may arise through solids containing alkali separating out during the distillative reprocessing of the butanediol. The optimum of alkali metal alcoholate to be added can be regulated in a simple manner by continuously checking the pH of the condensate to be treated. The pH should advantageously be above 9 and preferably from 10 to 12.

In general, the alkali metal alcoholate is employed in the form of a concentrated alcoholic solution. A solution of sodium methylate in methanol has proved particularly suitable. However, it is also possible to dissolve solid alkali metal alcoholate in butanediol and to use this solution for the treatment.

To permit very rapid dissolution of the insoluble solids in butanediol the treatment is carried out at an elevated temperature, which should be below the boiling point of butanediol at the particular minimum pressure used during the condensation. In practice, a temperature range of from 40 to 60° C., especially from 40° to 50° C., has proved advantageous and this readily permits the use of a pressure of from 0.5 to 2 mm Hg.

The process according to the invention for treating butanediol is particularly suitable for all polybutylene terephthalate processes in which the butanediol which distils off during the polycondensation is condensed in suitable injection condensers provided with a butanediol circulation system. In a continuous manufacturing process it is advantageous to admix the alkali metal alcoholates continuously, as an alcoholic solution, to the circulating butanediol. In batchwise operation it is also possible to add the alkali metal alcoholate solution in portions. Naturally, the stated concentration of alkali metal alcoholate or alkali metal hydride is maintained throughout the period of operation.

The dissolution of the solid constituents can advantageously be assisted by stirring or pumping.

We have found that the addition of alkali metal alcoholate or alkali metal hydride virtually completely eliminates the tendency of the equipment in question to corrode. Furthermore, we have found that purer butanediol than hitherto is recovered on distillative reprocessing. The butanediol can be re-used for the manufacture of polybutylene terephthalate.

The Examples which follow illustrate the process of the invention. Parts are by weight and bear the same relation to parts by volume as that of the kilogram to the liter. The percentages are by weight.

EXAMPLE 1

The starting material is butanediol which has been obtained as a condensate in the manufacture of polybutylene terephthalate and has a total solids content of 5%. The content of solids insoluble at room temperature is 2%. 1,000 parts of butanediol of the said quality are mixed, whilst stirring at from 55° to 60° C., with 1.7 parts of a 30% strength solution of sodium methylate in methanol (corresponding to 0.05% of Na methylate, based on butanediol) and the treatment is continued, in the same temperature range, whilst stirring. After a reaction time of 2 hours, the solids have completely dissolved, except for a slight opalescence. The pH of the solution, measured with a hydrogen electrode, is 11. The solution obtained no longer shows solid deposits after standing for one day at room temperature and is hence sufficiently stable for subsequent distillative reprocessing.

EXAMPLE 2

The procedure described in Example 1 is followed, but instead of sodium methylate 6 parts of a 10% strength solution of sodium ethylate in butanediol (corresponding to 0.06% based on total butanediol) are used. After stirring for 2 hours, the insoluble solids have dissolved virtually completely. The pH of the solution is 11.

COMPARATIVE EXPERIMENT 1

1,000 parts of butanediol, as described in Example 1, are used and 8.6 parts of a 50% strength aqueous sodium hydroxide solution (corresponding to 0.43% of NaOH based on butanediol) are added whilst stirring at from 55° to 60° C. After stirring for 2 hours, within the stated temperature range, the butanediol exhibits an unchanged heavy turbidity due to the presence of undissolved solid particles. Substantial amounts of insoluble solid separate out at the bottom of the vessel after standing for only 1 hour at room temperature.

COMPARATIVE EXPERIMENT 2

The procedure followed is as described in Comparative Experiment 1, but at from 65° to 70° C., and with the amount of sodium hydroxide added increased to 26 parts of a 50% strength by weight aqueous sodium hydroxide solution (corresponding to 1.3% of sodium hydroxide). After stirring for 2 hours at the stated temperature, the proportion of insoluble solid has virtually not diminished. After brief standing at room temperature, a substantial amount of solid settles out.

COMPARATIVE EXPERIMENT 3

Butanediol is treated, by the method described in Comparative Example 1, with 60 parts of a 20% strength aqueous sodium carbonate solution (corresponding to 1.2% of sodium carbonate). After stirrring for 2 hours, no dissolution of the solid constituents is observable.

COMPARATIVE EXPERIMENT 4

In the continuous manufacture of polybutylene terephthalate, 18 kg/hour of butanediol are obtained as a condensate in the precondensation and final condensation stages. In steady-state operation, this condensate contains about 5% of solids. The proportion of solids insoluble at room temperature is about 2%. The butanediol condensates from the precondensation and final condensation are combined in a single circuit which is connected to the injection condensers, used to strip off the vapors, of the precondensation and final condensation stages. The excess butanediol is taken off at regular intervals from a buffer vessel present in the circulation system. To maintain a flowable mixture, the material in the circulation system is periodically diluted with fresh butanediol. In spite of this measure, several of the injection nozzles on the condenser are blocked after a few days' operation and require mechanical cleaning. Furthermore, the pressure upstream from the nozzles rises continuously and the cooling capacity of the cooler present in the butanediol circulation system decreases substantially due to the cooling surfaces becoming covered with solids. After 4 weeks' operation, the lines require mechanical cleaning and the cooler has to be replaced, to allow it to be cleaned.

COMPARATIVE EXPERIMENT 5

The procedure followed is as described in Comparative Experiment 4, but 156 parts per hour of a 50% strength aqueous sodium hydroxide solution (corresponding to 0.43% of NaOH based on the butanediol produced) are fed continuously into a line of the butanediol circulation system, in which line the flow is turbulent, whilst maintaining a temperature of from 45° to 50° C. After a few days' operation, the butanediol in the circulation system is heavily contaminated with solids. The degree of clogging of the injection nozzles remains unchanged. The pressure upstream from the nozzles of the condensers increase progressively and the cooling capacity of the circulation cooler decreases progressively.

EXAMPLE 3

The procedure followed is as described in Comparative Example 5, but 35 g/hour of a 30% strength solution of sodium methylate in methanol (corresponding to 0.06% of sodium methylate based on butanediol) are added continuously to the butanediol circulation system. The butanediol in the system is kept at from 45° to 50° C. Periodic dilution of the circulating material with fresh butanediol is omitted. No deposition of solid is observed during operation of the installation, and in the course of 3 months' uninterrupted running no problems whatsoever due to solid depositing in the butanediol circulation system are encountered.

We claim:

1. A process for treating butanediol obtained as a condensate in the manufacture of polybutylene terephthalate, wherein an alkali metal alcoholate or alkali metal hydride is added to the condensate at an elevated temperature.

2. A process as claimed in claim 1, wherein from 0.01 to 0.2% by weight of an alkali metal alcoholate or alkali metal hydride is added.

3. A process as claimed in claim 1, wherein the pH is maintained at above 9.

4. A process as claimed in claim 1, wherein the temperature is maintained at from 40° to 60° C.

5. A process as claimed in claim 1, wherein a sodium alcoholate derived from an alkanol of 1 to 4 carbon atoms is used.

6. A process as claimed in claim 1, wherein sodium methylate is used.

* * * * *